(12) United States Patent
Picazo et al.

(10) Patent No.: US 9,113,691 B1
(45) Date of Patent: Aug. 25, 2015

(54) CLEANING SWABS FOR FINGERNAILS

(71) Applicants: Alejandra L. Picazo, Glendora, CA (US); Michael S. Farraj, Glendora, CA (US)

(72) Inventors: Alejandra L. Picazo, Glendora, CA (US); Michael S. Farraj, Glendora, CA (US)

(*) Notice: Subject to any disclaimer, the term of this patent is extended or adjusted under 35 U.S.C. 154(b) by 227 days.

(21) Appl. No.: 13/682,212

(22) Filed: Nov. 20, 2012

Related U.S. Application Data

(63) Continuation-in-part of application No. 12/900,001, filed on Oct. 7, 2010, now Pat. No. 8,337,913.

(51) Int. Cl.
*A61K 35/36* (2015.01)
*A61K 36/258* (2006.01)
*A61K 36/32* (2006.01)
*A61K 36/61* (2006.01)
*A45D 29/00* (2006.01)

(52) U.S. Cl.
CPC ................................. *A45D 29/00* (2013.01)

(58) Field of Classification Search
None
See application file for complete search history.

(56) References Cited

U.S. PATENT DOCUMENTS

| | | |
|---|---|---|
| 1,367,974 A | 2/1921 | Ivory |
| 1,667,570 A | 4/1928 | Thelander |
| 1,956,627 A | 5/1934 | Roth |
| 2,551,700 A * | 5/1951 | Pinco ............................ 132/75.6 |
| 4,547,363 A | 10/1985 | Joos |
| 4,886,078 A | 12/1989 | Shiffman |
| 4,930,529 A | 6/1990 | Whitney |
| 5,487,776 A | 1/1996 | Nimni |
| 5,806,537 A * | 9/1998 | Wittwer ........................ 132/200 |
| D416,688 S | 11/1999 | Baltierra |
| 6,102,048 A | 8/2000 | Baker |
| 6,153,208 A | 11/2000 | McAtee et al. |
| 6,342,208 B1 | 1/2002 | Hyldgaard et al. |
| 6,516,812 B2 | 2/2003 | Chang |
| 6,676,952 B2 | 1/2004 | Renimel et al. |
| 6,782,894 B2* | 8/2004 | Shum ............................ 132/200 |
| 8,034,891 B2 | 10/2011 | Okawa |
| 2007/0020220 A1 | 1/2007 | Osborne |
| 2007/0113864 A1* | 5/2007 | Vera ................................. 132/73 |
| 2007/0154575 A1 | 7/2007 | Shimoda et al. |
| 2007/0172431 A1 | 7/2007 | Galumbeck |
| 2008/0299060 A1* | 12/2008 | Bruno et al. ..................... 424/61 |
| 2009/0068128 A1 | 3/2009 | Waddington |
| 2009/0090375 A1* | 4/2009 | Tran ............................. 132/73.5 |
| 2009/0090377 A1* | 4/2009 | Tran ............................. 132/75.3 |
| 2009/0183327 A1 | 7/2009 | Karie |
| 2009/0274770 A1 | 11/2009 | Gammelsaeter et al. |
| 2011/0250227 A1 | 10/2011 | Elraz |
| 2013/0324948 A1* | 12/2013 | Baschnagel .................. 604/289 |

* cited by examiner

Primary Examiner — Chris R Tate

(57) ABSTRACT

The present invention features a cleaning swab for cleaning, disinfecting, and sealing underneath fingernails. The swab features an elongated shaft having a first end and a second end. A first swab is disposed on the first end of the elongated shaft. The first swab is impregnated with a solution with at least six of the following: keratin, *equisetum arvense*, carrageenan, *aucoumea klaineana* extract, ginseng root extract, vitamin C, and tea tree oil. The first swab has an oval cone profile with a hard sharp pointed tip and indentation grooves disposed on the lateral surface of the swab.

1 Claim, 4 Drawing Sheets

CLEANING SWABS FOR FINGERNAILS

CROSS REFERENCE

This application claims priority to U.S. Non-Provisional application Ser. No. 12/900,001 filed Oct. 7, 2010 as a continuation-in-part, the specification of which is incorporated herein by reference in its entirety.

FIELD OF THE INVENTION

The present invention is directed to a personal hygiene tool, more particularly to a cotton swab with a novel cleaning solution for cleaning, disinfecting, and sealing underneath fingernails.

BACKGROUND OF THE INVENTION

To clean under one's fingernails, individuals generally use a thin piece of metal or wood to scrap dirt from under the nail. The present invention features cleaning swabs with a novel cleaning solution for cleaning, disinfecting, and sealing underneath fingernails. The swabs of the present invention can help promote good personal hygiene as well as help prevent infections occurring in and around the fingernail. The swabs may be available (or used) in a variety of locations including but not limited to hospitals, vehicles, convenience stores, hospitality locations such as hotels and motels, nail salons, homes, work places, and the like. The swabs may be packaged in dispensers or individual packets (wrappers).

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

Figure 1:
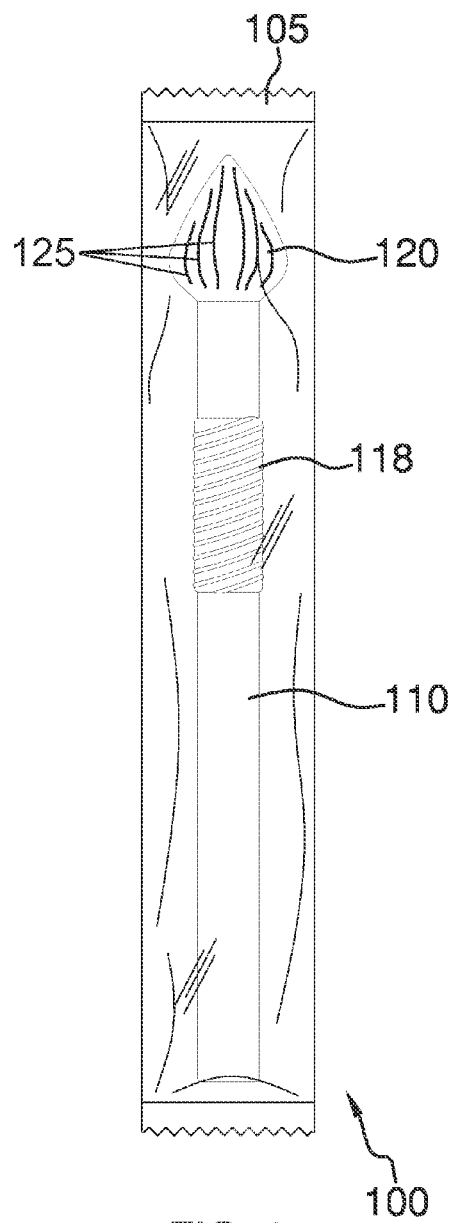
FIG. 1 is a side view of a swab of the present invention as wrapped in a wrapper.
Figure 2:
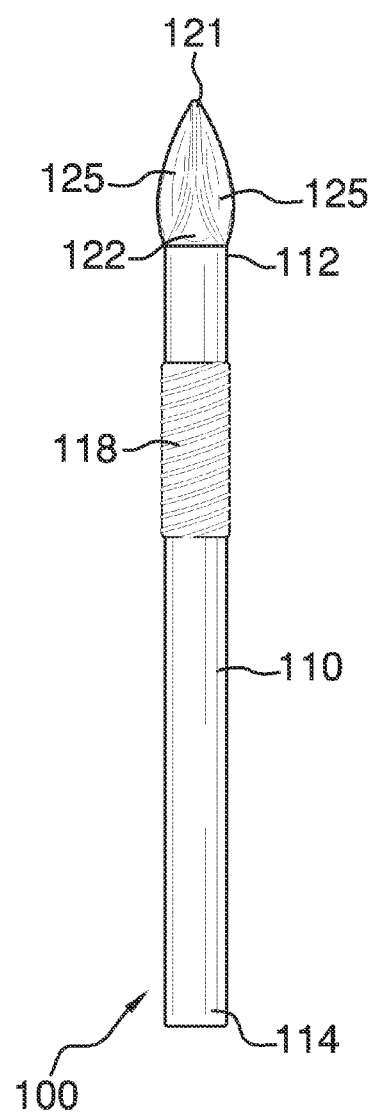
FIG. 2 is a side view of a swab tool of the present invention.
Figure 3:
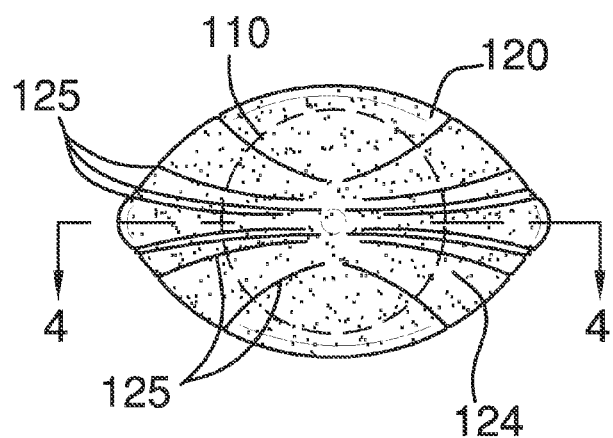
FIG. 3 is a top view of the swab tool of FIG. 2.

Referring now to FIG. 1-7, the present invention features a cleaning swab tool (100) with a novel cleaning solution for cleaning, disinfecting, and sealing underneath fingernails. The cleaning swab tool (100) may be available (or used) in a variety of locations including but not limited to hospitals, vehicles, convenience stores, hospitality locations such as hotels and motels, nail salons, and the like. The cleaning swab tool (100) may be packaged in dispensers or individual packets (wrappers 105).

The cleaning swab tool (100) of the present invention comprise an elongated shaft (110) having a first end (112) and a second end (114). A gripping component (118) may be disposed on the shaft (110), for example near the first end, in or around the middle, and/or near the second end. Removably disposed on at least the first end is a first swab (120). The swab (120) has a general oval cone profile with a hard sharp pointed tip (121), a base (122) and a lateral surface (124). The hard sharp pointed tip (121) enables a user to remove some hard debris or dirt from the fingernails with ease. The oval cone profile enable the swab to reach deeper areas beneath a fingernail thus offers better cleaning effects.

In some embodiments, the first swab (120) is pre-soaked with a solution (160) for cleaning, disinfecting, and sealing (e.g., helping to prevent accumulation of dirt, debris, and oil) underneath the fingernail. In some embodiments, the first swab (120) is made of cotton, non-woven fabrics, or microfibers.

In some embodiments, the first swab (120) comprises a plurality of indentation grooves (125) disposed on the lateral surface (124), wherein the indentation grooves (125) extend from the base (122) toward the sharp pointed tip (121), wherein the grooves (125) is configured to function as duct for fingernail dirt/debris release.

In some embodiments, the cleaning swab tool further comprise a magnifying component (130), wherein the magnifying component (130) has a first arm (132) with a first end (200) and a second end (201), a second arm (134) with a first end (202) and a second end (203), and a magnifying glass (136) supported by the first arm (132) and the second arm (134). The magnifying glass (136) enables a user to see his/her fingernail in a more detailed view and thus offers a capacity of more thorough cleaning work. The first end (200) of the first arm (132) and the first end (202) of the second arm (134) are pivotably disposed on the elongated shaft (110) near the first end (112) of the shaft, wherein the magnifying component (130) is pivotably moveable between a storage position and a deployed position, wherein in the storage position, the first arm (132) and the second arm (134) are collapsed toward the shaft (110) and the magnifying glass (136) contacts the shaft, wherein in the deployed position, the first arm (132) and the second arm (134) are deployed hovering above the first swab (120) with the magnifying lens (136) at a predetermined distance away from the first swab. In some embodiments, the magnifying lens (136) is pivotably disposed at the second end (201) of the first arm (132) and the second end (203) of the second arm (134), wherein the magnifying lens (136) can rotate up to 360°.

In some embodiments, the first arm (132) and the second arm (134) are removably disposed on the elongated shaft (110) near the first end (112) of the shaft. The first arm (132) and the second arm (134) are made of hard plastic and can be bent outward slightly to disengage from the elongated shaft (110). Such arrangement would enable a user to use the magnifying component (130) on a needed basis.

In some embodiments, the predetermined cross angle is between 90 and 150 degree. In some embodiments, the predetermined distance is between 1 inch and 5 inches. In some embodiments, the predetermined distance is between 5 inch and 10 inches. In some embodiments, the magnifying glass (136) has a focus length of 25 cm.

In some embodiments the solution (160) comprises one or more (at least one) of the following: keratin (e.g., hydrolyzed keratin), horsetail extract (e.g., *equisetum arvense*), carrageenan, *aucoumea klaineana* extract, ginseng root extract, vitamin C (e.g., sodium ascorbyl phosphate), and tea tree (e.g., oil). In some embodiments the solution (160) comprises two or more (at least two) of the following: keratin (e.g.; hydrolyzed keratin), horsetail extract (e.g., *equisetum arvense*), carrageenan, *aucoumea klaineana* extract, ginseng root extract, vitamin C (e.g., sodium ascorbyl phosphate), and tea tree (e.g., oil). In some embodiments the solution (160) comprises three or more (at least three) of the following: keratin (e.g., hydrolyzed keratin), horsetail extract (e.g., *equisetum arvense*), carrageenan, *aucoumea klaineana* extract, ginseng root extract, vitamin C (e.g., sodium ascorbyl phosphate), and tea tree (e.g., oil). In some embodiments the solution (160) comprises four or more (at least four) of the following: keratin (e.g., hydrolyzed keratin), horsetail extract (e.g., *equisetum arvense*), carrageenan, *aucoumea klaineana* extract, ginseng root extract, vitamin C (e.g., sodium ascorbyl phosphate), and tea tree (e.g., oil). In some embodiments the solution (160) comprises five or more (at least five) of the following: keratin (e.g., hydrolyzed keratin), horsetail extract (e.g., *equisetum arvense*), carrageenan, *aucoumea klaineana* extract, ginseng root extract, vitamin C (e.g., sodium ascorbyl phosphate), and tea tree (e.g., oil). In some embodiments the solution (160) comprises six or more (at least six) of the following: keratin (e.g., hydrolyzed keratin), horsetail extract (e.g., *equisetum arvense*), carrageenan, *aucoumea klaineana* extract, ginseng root extract, vitamin C (e.g., sodium ascorbyl phosphate), and tea tree (e.g., oil). Optionally, the solution (160) further comprises other proteins (e.g., peptides). Without wishing to limit the present invention to any theory or mechanism, it is believed that tea tree oil may help as an antibacterial and/or an antifungal component in the solution (160).

In some embodiments, the solution (160) comprises the following amino acids: Aspartic Acid (Asp), Glutamic Acid (Glu), Serine (Ser), Glycine (Gly), Histidine (His), Argenine (Arg), Threonine (Thr), Alanine (Ala), Proline (Pro), Tyrosine (Tyr), Valine (Val), Methionine (Met), Lanthionine (Lan), Isoleucine (Ile), Leucine (Leu), Phenylalanine (Phe), Lysine (Lys), and Cystine (Cys). In some embodiments, the percentage of Aspartic Acid (Asp) is between about 5 to 10%, for example 6.6%. In some embodiments, the percentage of Glutamic Acid (Glu) is between about 10 to 15%, for example 14.2%. In some embodiments, the percentage of Serine (Ser) is between about 10 to 15%, for example 10.7%. In some embodiments, the percentage of Glycine (Gly) is between about 5 to 10%, for example 8.3%. In some embodiments, the percentage of Histidine (His) is between about 0.1 to 5%, for example 0.7%. In some embodiments, the percentage of Argenine (Arg) is between about 5 to 10%, for example 7%. In some embodiments, the percentage of Threonine (Thr) is between about 5 to 10%, for example 6.4%. In some embodiments, the percentage of Alanine (Ala) is between about 5 to 10%, for example 7.3%. In some embodiments, the percentage of Proline (Pro) is between about 5 to 10%, for example 6.6%. In some embodiments, the percentage of Tyrosine (Tyr) is between about 0.5 to 5%, for example 1.6%.

In some embodiments, the percentage of Valine (Val) is between about 5 to 10%, for example 6.9%. In some embodiments, the percentage of Methionine (Met) is between about 0.01 to 1%, for example 0.1%. In some embodiments, the percentage of Lanthionine (Lan) is between about 0.1 to 5%, for example 0.5%. In some embodiments, the percentage of Isoleucine (Ile) is between about 1 to 5%, for example 3.8%. In some embodiments, the percentage of Leucine (Leu) is between about 5 to 10%, for example 8.8%. In some embodiments, the percentage of Phenylalanine (Phe) is between about 1 to 5%, for example 2.4%. In some embodiments, the percentage of Lysine (Lys) is between about 1 to 5%, for example 2.4%. In some embodiments, the percentage of Cystine (Cys) is between about 2 to 10%, for example 4.8%.

Figure 4:
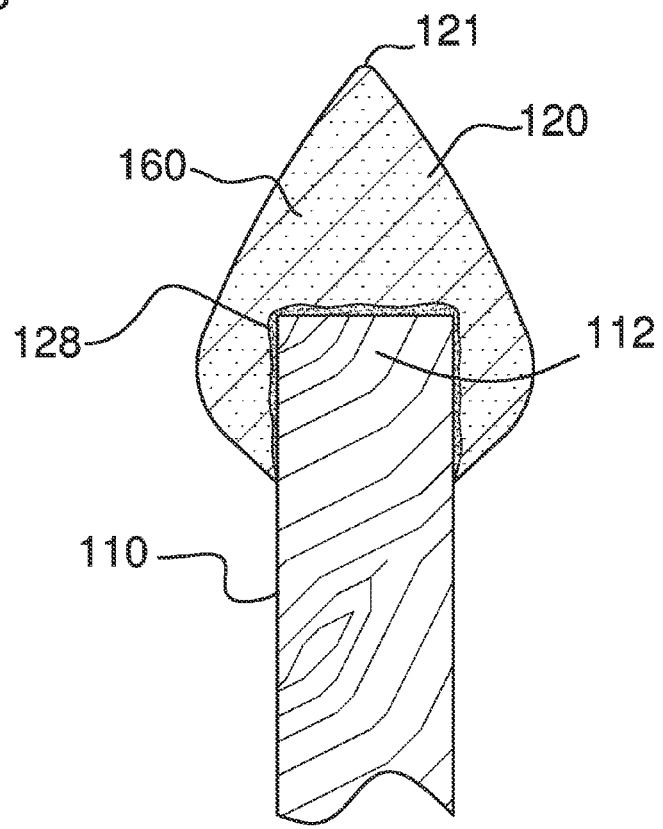
FIG. 4 is a cross sectional view of the swab tool of FIG. 3.
Figure 5:
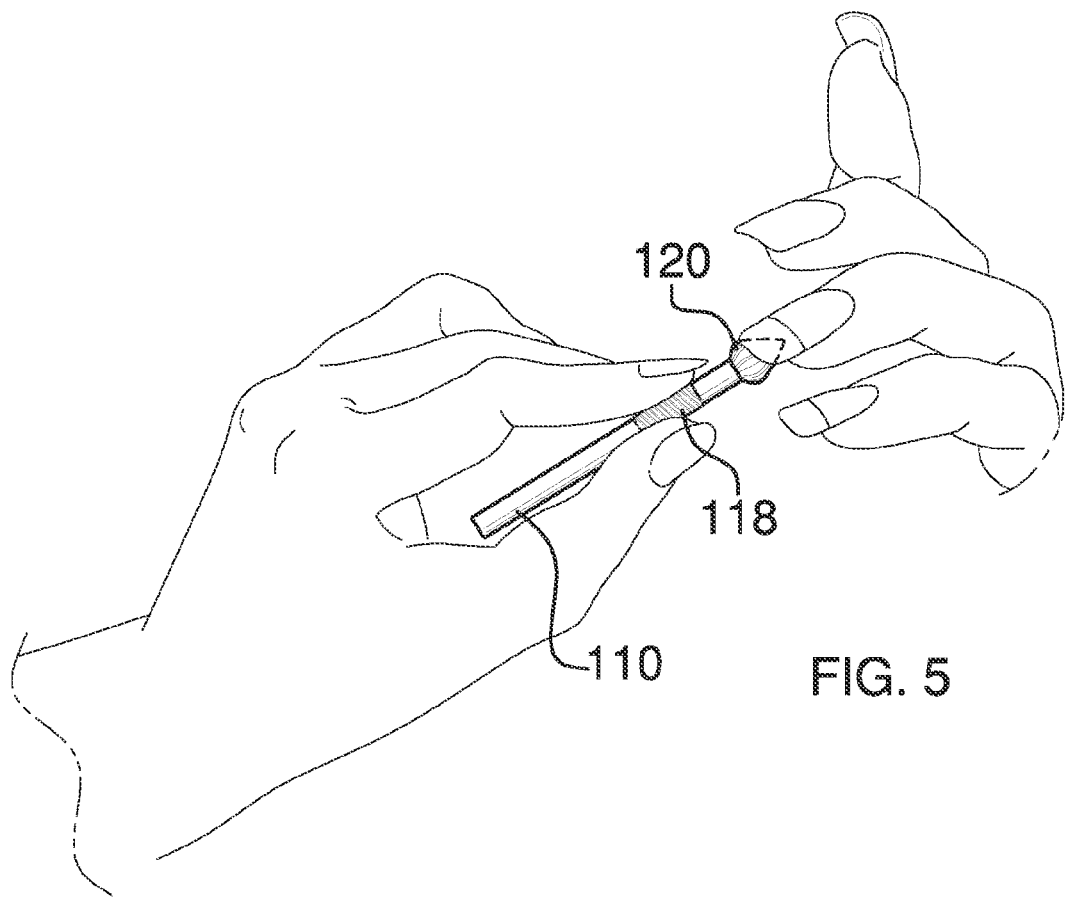
FIG. 5 is an in-use view of the swab tool of the present invention. To use the swab, simply sweep the absorbent component with the cleaning solution underneath the nail to help remove dirt and debris (and disinfect and seal).
Figure 6:
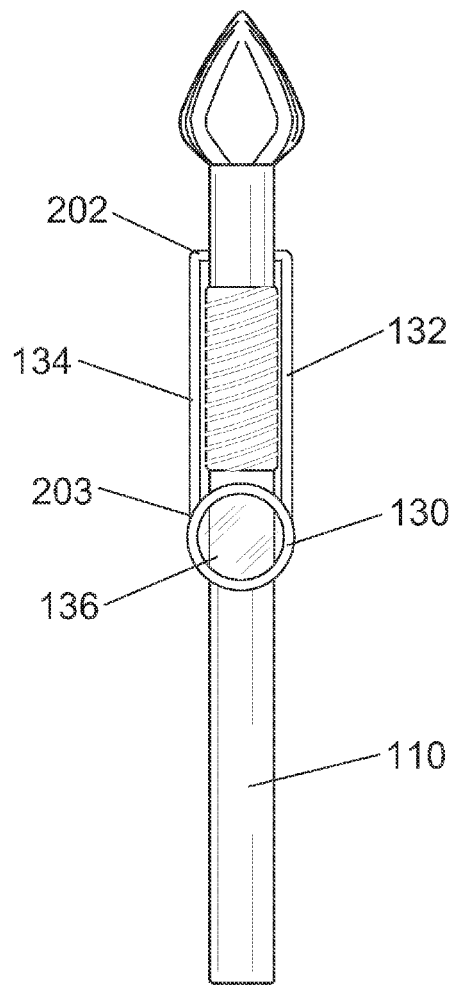
FIG. 6 is a front view of the swab tool with a magnifying component.
Figure 7:
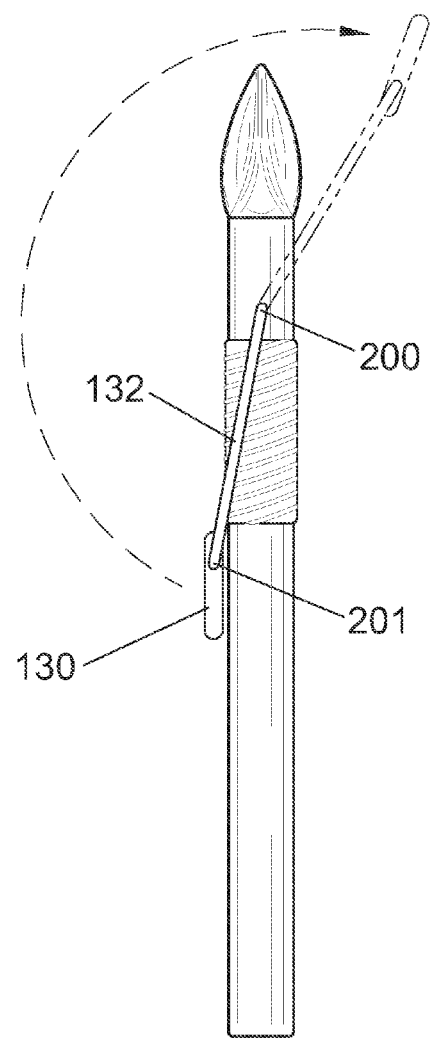
FIG. 7 is a side view of the swab tool with a magnifying component.

As shown in FIG. 4, the first swab (120) may be attached to the first end (112) of the shaft (110) via an adhesive (128). In some embodiments, a second swab is disposed on the second end (114) of the shaft (110).

The swab tool (100) of the present invention may be constructed in a variety of shapes and sizes. In some embodiments, the shaft (110) is between about 1 to 2 inches in height as measured from the first end to the second end. In some embodiments, the shaft (110) is between about 2 to 3 inches in height as measured from the first end to the second end. In some embodiments, the shaft (110) is between about 3 to 5 inches in height as measured from the first end to the second end. In some embodiments, the shaft (110) is more than about 5 inches in height as measured from the first end to the second end.

As used herein, the term "about" refers to plus or minus 10% of the referenced number. For example, an embodiment wherein the shaft (110) is about 5 inches in height includes a shaft (110) that is between 4.5 and 5.5 inches in height.

The disclosures of the following U.S. Patents are incorporated in their entirety by reference herein: U.S. Pat. No. 4,886,078: U.S. Pat. Application No. 2009/0183327: U.S. Pat. Application No. 2007/0113864: U.S. Pat. No. 1,667,570; U.S. Pat. No. 4,930,529; U.S. Pat. No. 1,956,627: U.S. Pat. No. 6,516,812; U.S. Pat. No. 6,102,048; U.S. Design Pat. No. D416,688: U.S. Pat. No. 1,367,974.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A method of cleaning, disinfecting, and sealing underneath fingernails with a cleaning swab tool, wherein the method comprises:
    (a) grabbing an elongated shaft (110), wherein the shaft has a first end (112) and a second end (114), wherein a first swab (120) is removably disposed on at least the first end (112) of the elongated shaft (110), wherein the first swab (120) has a hard sharp pointed tip (121), wherein the first swab (120) has a general oval cone profile with a base (122) and a lateral surface (124); and
    (b) sweeping the first swab (120) underneath the nail to help remove dirt and debris;
wherein the first swab (120) is pre-soaked with a solution comprising at least six of the following: keratin, *equisetum arvense*, carrageenan, *aucoumea klaineana* extract, ginseng root extract, vitamin C, and tea tree oil.

* * * * *